United States Patent [19]

Cadossi et al.

[11] Patent Number: 5,276,428
[45] Date of Patent: Jan. 4, 1994

[54] CONTACT DETECTING AND SIGNALING DEVICE

[75] Inventors: Ruggero Cadossi; Donata Marazzi, both of Carpi, Italy

[73] Assignee: IGEA S.r.l., Carpi, Italy

[21] Appl. No.: 829,971

[22] Filed: Feb. 3, 1992

[30] Foreign Application Priority Data

Feb. 5, 1991 [IT] Italy .................. TO91 A 000070
Jul. 31, 1991 [IT] Italy .................. TO91 A 000608

[51] Int. Cl.$^5$ .................................. G08B 21/00
[52] U.S. Cl. ................................... 340/540; 128/897; 340/573; 340/605; 340/647
[58] Field of Search ............... 340/540, 573, 647, 604, 340/605, 680; 128/897, 898

[56] References Cited

U.S. PATENT DOCUMENTS

| | | | |
|---|---|---|---|
| 4,023,156 | 5/1977 | Galvin | 340/550 |
| 4,956,635 | 9/1990 | Langdon | 340/540 |
| 4,983,954 | 1/1991 | Huston | 340/657 |
| 5,036,309 | 7/1991 | Dennison, Jr. | 340/540 |
| 5,056,235 | 10/1991 | Thomas | 340/680 |

FOREIGN PATENT DOCUMENTS

| | | |
|---|---|---|
| 0011204 | 5/1980 | European Pat. Off. . |
| 0407368 | 1/1991 | European Pat. Off. . |
| 2208300 | 6/1974 | France . |
| 2589609 | 7/1987 | France . |
| 1605023 | 12/1981 | United Kingdom . |

*Primary Examiner*—Glen R. Swann
*Attorney, Agent, or Firm*—Ladas & Parry

[57] ABSTRACT

A portable generator generates a predetermined signal and has an output connected to a first transducer for transmitting the above signal to the body of a first operator (e.g. physician, nurse, etc.); and processing means for analyzing a signal picked up by a second transducer on a second operator (e.g. a patient, etc.) and detecting the significant presence of the above predetermined signal, as a consequence, for example, of direct or indirect contact between the first operator and the second operator.

25 Claims, 4 Drawing Sheets

CONTACT DETECTING AND SIGNALING DEVICE

BACKGROUND OF THE INVENTION

The present invention relates to a contact detecting and signaling device.

In particular, but not exclusively, the present invention relates to a device for detecting and signaling skin contact (direct or indirect, e.g. via a tool, such as a pair of scissors or the overall) between two parties, e.g. a physician and patient.

Numerous medical activities, such as operations, dental work, or routine surgery work (infectious or not) are known to demand certain precautions, such as the use of gloves, to safeguard both parties (physician and patient) against infection caused by direct skin contact.

The use of gloves, however, has not proved a hundred percent reliable in preventing the transmission of germs or similar. In the course of an operation, in fact, any porosity or even minor inadvertent puncturing of the gloves results in contact between the patient's blood and the skin of the surgeon, with obvious consequences, particularly in the case of operations lasting several hours.

Additional risk is also encountered at the medication stage, at which the patient is attended by the physician or nurse for long periods of time, and with the aid of instruments (syringes, scissors, etc.) by which the gloves may easily be punctured.

Nor is the above situation limited to the medical field. Certain machine operators are also required to wear gloves, any porosity or puncturing of one or both of which, if not detected immediately, may result in serious consequences for the operator.

SUMMARY OF THE INVENTION

It is an object of the present invention to provide a device for detecting and signaling contact between two operators, or between an operator and machine, designed to indicate such contact immediately and so enable appropriate steps to be taken.

According to the present invention, there is provided a device for detecting direct or indirect contact between at least one first operator and a second operator (or machine), characterised by the fact that it comprises:

means for generating a predetermined signal;
first transducer means for transmitting said predetermined signal to the body of said first operator;
second transducer means fittable to the body of said second operator (or the structure of said machine) for picking up respective signals present in the same; and
processing means connected to said second transducer means, for analyzing the signals picked up by said second transducer means and so detecting and indicating the significant presence of said predetermined signal.

BRIEF DESCRIPTION OF THE DRAWINGS

Two preferred non-limiting embodiments of the present invention will be described by way of example with reference to the accompanying drawings, in which.

DETAILED DESCRIPTION OF THE INVENTION

Figure 1:
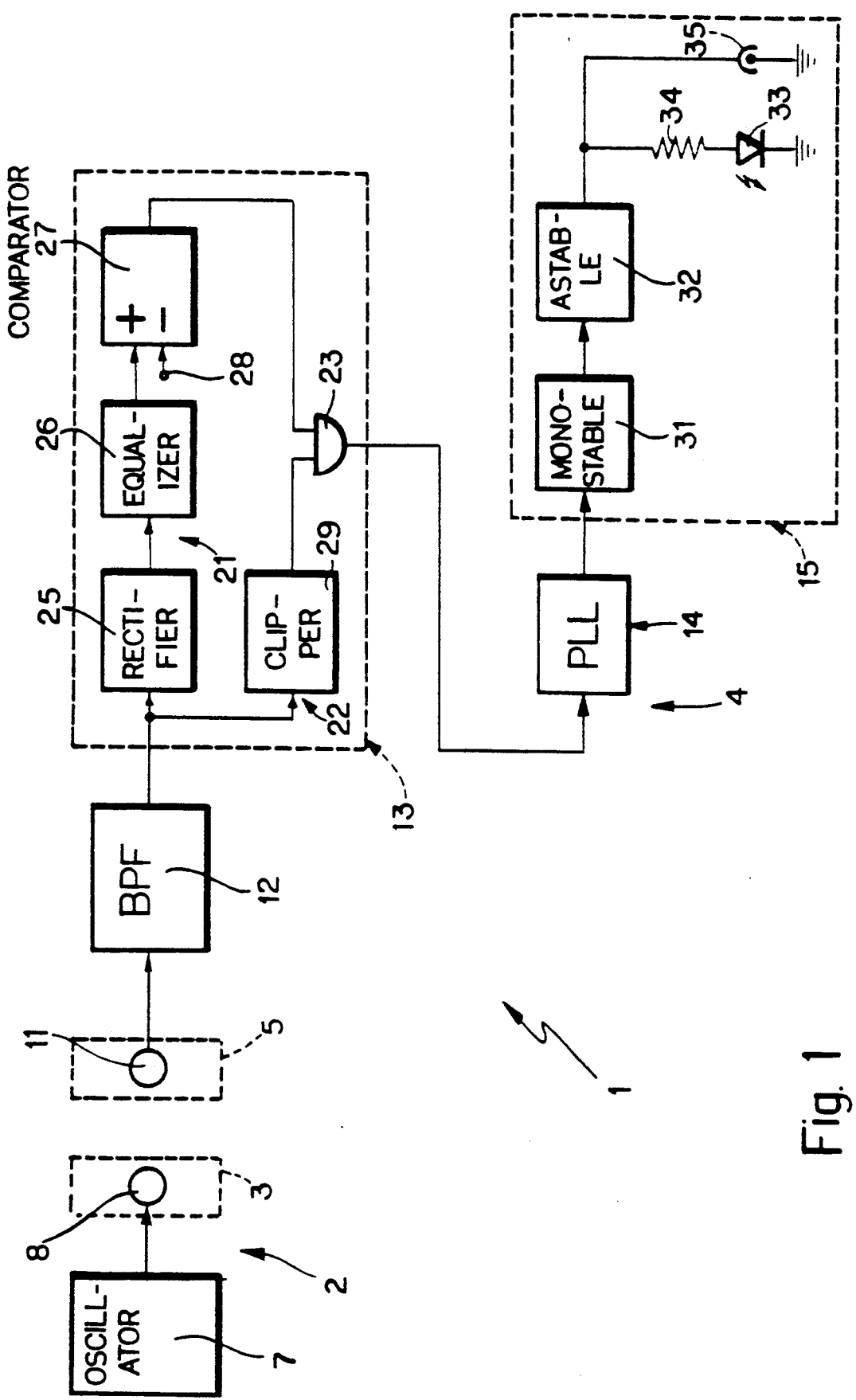
FIG. 1 shows a block diagram of a first embodiment of a device in accordance with the present invention.

Number 1 in FIG. 1 indicates a detecting and signaling device in accordance with the present invention, said device substantially comprising a transmitting unit 2 fittable to a first operator 3; and a receiving and processing unit 4 fittable to a second operator 5.

Transmitting unit 2 substantially comprises an oscillator 7, preferably for producing an alternating squarewave or even more complex signal having a predetermined frequency conveniently in, but not necessarily limited to, the audio frequency band. Said alternating signal preferably ranges between 200 Hz and 1 kHz, which is a good compromise between the need for an operating frequency which, on the one hand, is low enough to reduce the capacity effect between physician and patient, and, on the other, is sufficiently greater than the mains frequency (50–60 Hz) for enabling effective filtration of conducted interference. The signal produced by oscillator 7 is preferably based in known manner on a quartz signal (not shown) for obtaining an accurate, stable frequency value.

Transmitting unit 2 also comprises a transducer 8 for transmitting the signal produced by oscillator 7 to the body of operator 3, and preferably consisting of an electrode of the type commonly used in the medical field, e.g. for picking up electrocardiographic signals.

Receiving and processing unit 4 substantially comprises:

a transducer 11 fittable to the body of operator 5 for picking up electric signals present in the same, and conveniently of the same type described in connection with transducer 8;

a preferably active band-pass filter (amplifier) 12 consisting, for example, of a first low-pass filter with a cutoff frequency of around 1 kHz, cascade-connected to a high-pass filter with a cutoff frequency of around 200 Hz;

a circuit 13 for processing the output signal from filter 12;

a check circuit 14 for determining the presence of a frequency equal to that of the signal emitted by oscillator 7;

a signaling circuit 15 enabled by check circuit 14.

Circuit 13 substantially presents two branches 21 and 22 having their inputs connected to the common output of filter 12, and their outputs connected to respective inputs of a two-input AND circuit 23.

Branch 21 comprises, in cascade formation, a rectifying circuit 25, an equalizing circuit 26, and a non-inverting comparator circuit 27, which compares the signal from equalizing circuit 26 with a continuous reference signal present at terminal 28 and conveniently produced by means of a potentiometer (not shown). The output of comparing circuit 27 is therefore high whenever the input signal exceeds a predetermined threshold value, which occurs whenever the amplitude of the signal from transducer 11, having a frequency in the band defined by filter 12, exceeds a predetermined minimum value.

Branch 22 substantially consists of a clipping circuit 29 which, in the more likely case of a sinusoidal signal from transducer 11, produces a square wave, obviously of the same frequency as the sinusoidal signal, and preferably oscillating between high and low levels compatible with the signals acceptable by AND circuit 23

Circuit 14 is a known "phase locked loop" circuit currently manufactured, for example, by MOTOROLA and marketed under part number 4046. By means of conventional circuitry, the output of circuit 14 supplies a recognition signal, e.g. high level, whenever the frequency of the input signal is close to the set frequency value (or narrow range of frequency values) of circuit 14.

Signaling circuit 15 comprises a monostable circuit 31 followed by an astable circuit 32, the output of which controls a LED 33 via a resistor 34, and a buzzer 35.

Figure 2:
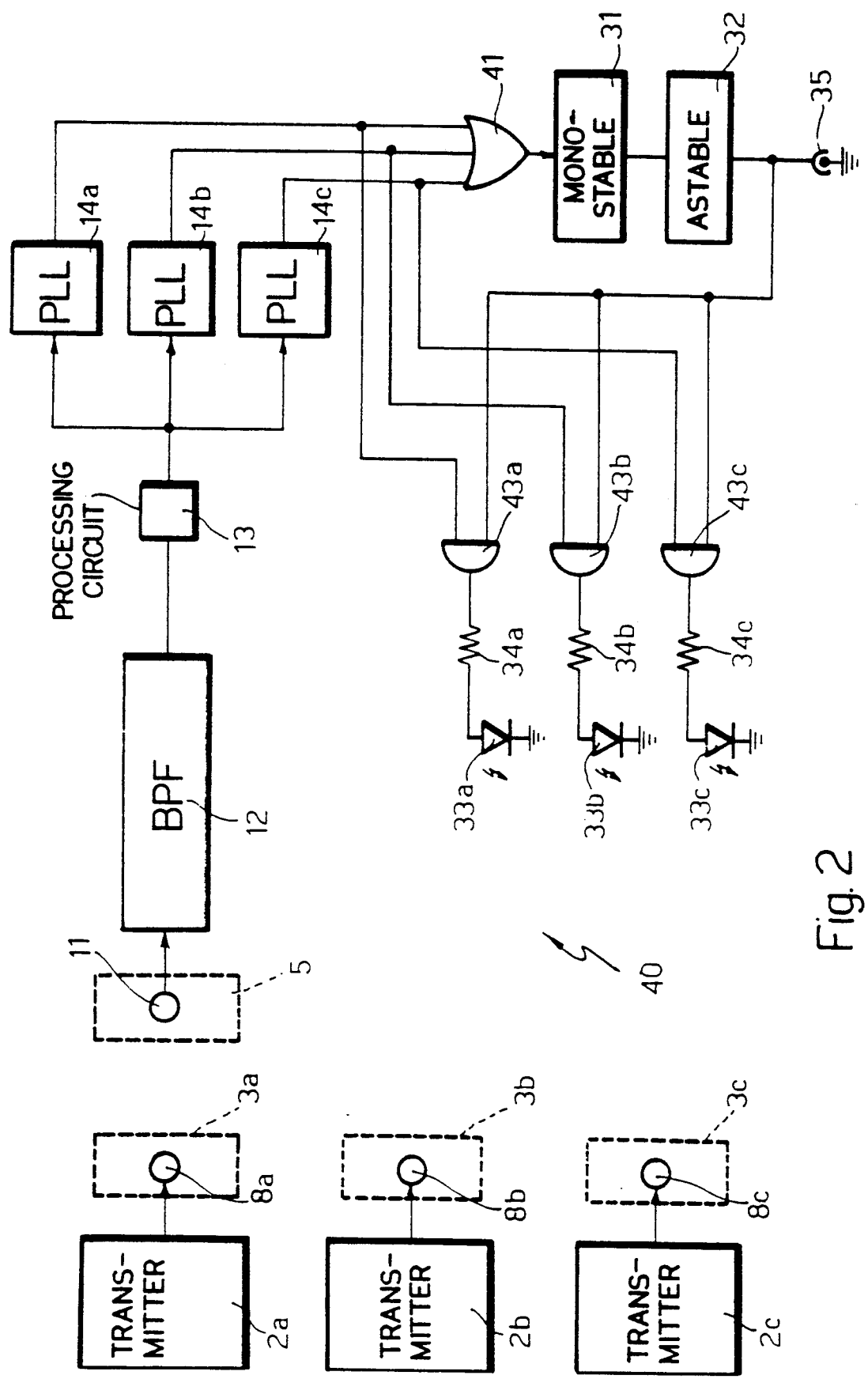
FIG. 2 shows a block diagram of a second embodiment of a device in accordance with the present invention.

Number 40 in FIG. 2 indicates a detecting and signaling device also in accordance with the present invention, and the parts identical or at least equivalent to those described with reference to FIG. 1 are shown, for the sake of simplicity, using the same reference numbers accompanied by the letters a, b, c.

The first point to note is that device 40 comprises a number of transmitting units 2a, 2b, 2c, each of which emits a signal of a respective frequency (e.g. fa, fb, fc) and is connected to a respective transducer 8a, 8b, 8c fittable to a respective operator 3a, 3b 3c.

Provision is made for one receiving and processing unit, which substantially presents:
transducer 11 fitted to operator 5;
band-pass filter 12;
signal processing circuit 13;
three check circuits 14a, 14b, 14c for detecting the presence of signals having respective frequencies fa, fb, fc;
a three-input OR circuit 41 connected respectively to the outputs of circuits 14a, 14b, 14c;
monostable and astable circuits 31 and 32 cascade-connected downstream from OR circuit 41;
buzzer 35 connected to the output of astable circuit 32;
three two-input AND circuits 43a, 43b, 43c, one input of which is connected to the output of respective check circuit 14a, 14b, 14c, and the second input of which is connected to the output of astable circuit 32;
three LED's 33a, 33b, 33c connected via resistors 34a, 34b, 34c to respective outputs of AND circuits 43a, 43b, 43c.

Device 1 operates as follows.

Transmitting unit 2 is fitted to the body of operator 3, who thus provides for transmitting a given frequency.

Transducer 11 is fitted to the body of operator 5, and the signals picked up from the same are filtered and, if necessary, amplified by band-pass filter 12 for separating the operating signal from any interference of a different frequency produced by the body of operator 5.

Processing circuit 13 analyzes the amplitude of the signal from transducer 11, which amplitude is much higher in the event of skin contact between the two operators, either direct or indirect, via an instrument, such as scissors, etc., or through a punctured glove or liquid (blood, etc.) seeping into the same. When said amplitude exceeds the set threshold, the signal (clipped by circuit 29) is sent to the input of circuit 14.

Circuit 14 determines whether the frequency of the input signal corresponds with its own frequency setting (equal to the frequency of the signal produced by oscillator 7), and, if it does, enables monostable circuit 31 which in turn enables astable circuit 32 for a given length of time, e.g. 10 seconds. Astable circuit 32 therefore provides for intermittently supplying, e.g. at 5 Hz frequency, both LED 33 and buzzer 35, to inform operator 3 that a potential risk situation has been detected.

Device 10 operates in exactly the same way as device 1, the only difference being, obviously, that it caters to a number of operators attending simultaneously to the same patient. As such, it is particularly useful for team work, such as a surgical operation conducted by a surgeon assisted by other physicians and/or specialized personnel.

Figure 3:
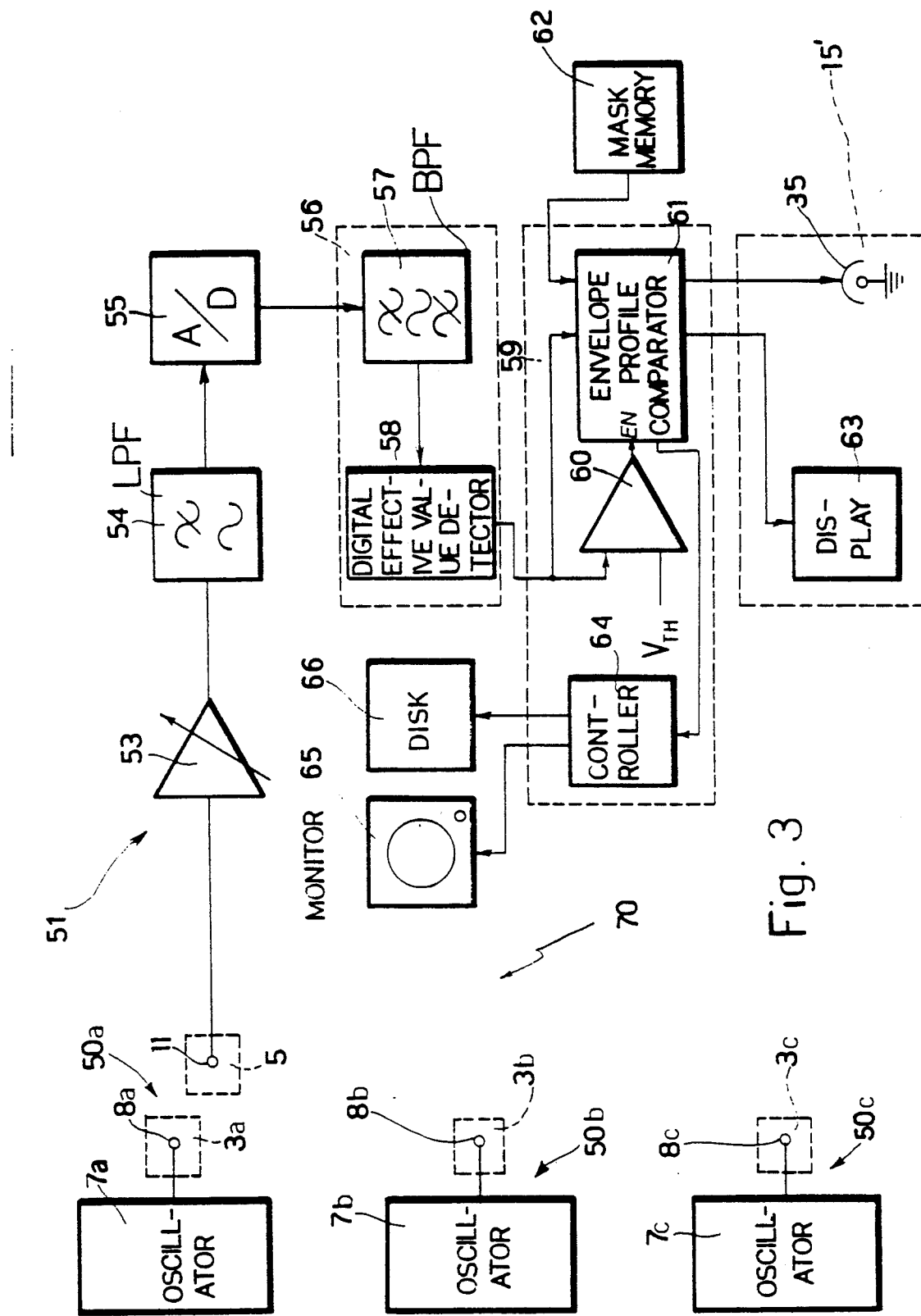
FIG. 3 shows a block diagram of a third embodiment of a device in accordance with the present invention.

Number 70 in FIG. 3 indicates a further embodiment of the device according to the present invention. As in the FIG. 2 embodiment, device 70 presents a number of transmitting units 50a, 50b, 50c fittable to respective operators 3a, 3b, 3c, and comprising respective oscillators 7a, 7b, 7c for emitting signals of respective frequencies fa, fb, fc, and connected to respective transducers 8a, 8b, 8c. In this case also, provision is made for one receiving and processing unit 51 substantially comprising:

transducer 11 fitted to operator 5;
a variable-gain amplifier 53;
a low-pass filter 54 with a cutoff frequency of 3.5 KHz;
a 16-bit analog/digital converter 55;
a programmable device 56 defining:
  a selective digital band-pass filter 57 having a variable middle frequency tunable sequentially to n frequencies generated by the transmitting unit oscillators (in the example shown, filter 57 is tunable to the three frequencies fa, fb, fc generated by oscillators 7a, 7b, 7c);
  a digital effective value detector 58 for sequentially producing n output signals, each having the envelope of the respective output signal of filter 57;
a microprocessor 59 (e.g. an N.E.C. V-25 type) defining:
  a threshold comparator 60 for analyzing, point by point, the amplitude of the signal from detector 58, comparing it with a potential-contact threshold $V_{TH}$, and, in the event the threshold is exceeded, supplying an enabling signal;
  an evelope profile comparator 61, which, when enabled by threshold comparator 60, memorises the time curve of the effective value supplied by detector 58, and compares it with a reference mask stored in memory 62;
  a circuit 64 controlling a monitor 65 and an external mass storage memory 66 (in particular, a disk storage memory, the disks of which can be stored and retrieved when needed);
signaling circuit 15' comprising:
  a buzzer 35; and
  a display 63 showing the alarm status and which of the n operators (in this case, 3a, 3b, 3c) has activated the alarm.

The FIG. 3 device operates as described with reference to FIGS. 1 and 2, except that contact is detected also on the basis of the shape of the incoming signal. In the event of direct or indirect contact between operator and patient, in fact, the signal has been found to present a characteristic, repetitive time curve. That is, the amplitude of the signal, which, in the event of contact, exceeds a threshold which would otherwise rarely be reached, presents a maximum level upon contact, and falls off to produce a typical curve which is repeated at each successive contact.

The signal from transducer 11 is therefore first amplified in 53, then filtered by low-pass filter 54, converted to digital form in 55, and filtered sequentially and at high speed by high-selectivity filter 57, so as to "simultaneously" control n signals with fairly close frequencies (e.g. 200 Hz apart, between 200 and 1000 Hz). The output signals from filter 57 are then processed by detector 58 to obtain the envelope of the signals picked up by transducer 11.

The amplitude of the resulting envelope is compared and, if any point exceeds threshold $V_{TH}$, the envelope is compared with a previously stored reference mask relative to the typical fall-off curve. If the incoming signal envelope matches the memorised mask (or falls within appropriate tolerances), contact is determined, and the microprocessor activates buzzer 35 and display 63. Display 63 may be as shown in FIG. 2, featuring a number of LED's 33a, 33b, 33c relative to respective operators 3a, 3b, 3c, or a display showing the number of the operator contacted, who is identified on the basis of the frequency data in the output signal from filter 57, which data is memorised together with the signal during subsequent processing by components 59–61.

The FIG. 3 device also presents a monitor 65 for monitoring, for example, the operation and also visually controlling the signal processed by detector 58, as well as any direct or indirect contact situations. Said signal and the output from comparator 61 are also sent to memory 66 for enabling permanent storage of the course of each operation. The information so stored may be employed to advantage, even years later, in the event of the patient or operator developing diseases suspected of originating in the course of the operation in question, thus enabling accurate long-term reconstruction of the operation, direct treatment, and also statistical data collection, e.g. for evaluating the safety of gloves or specific operating procedures.

The advantages of the devices according to the present invention will be clear from the foregoing description. The high degree of sensitivity of devices 1, 40 and 70, in fact, provides for immediately detecting even the slightest skin contact, such as that caused by accidental puncturing of a glove during an operation.

To those skilled in the art it will be clear that changes may be made to devices 1, 40 and 70 as described and illustrated herein without, however, departing from the scope of the present invention.

For example, transmitting unit 2, which must obviously be provided with a supply battery enabling it to operate independently for a reasonable length of time, may be provided with a monitor for supplying a signal, e.g. an intermittent sound signal, indicating that the battery is about to run down.

Numerous circuit configurations equivalent to or even more complex than those described above may also be employed featuring, for example, microprocessor circuits.

It should be pointed out that the above devices may also be employed, with no alterations required, in other than the medical field, e.g. for detecting and signaling direct or indirect contact, via any type of tool, between a machine operator and machine. In this case, care must obviously be taken to ensure transducer 11 is so located on the machine structure as to ensure the best possible signal is picked up.

The transmitting unit/s 2, 2a, 2b, 2c may generate single pulses or, preferably, trains of pulses. In the latter case, contact may be recognized also from the length of the received train. To this end, the devices of FIGS. 1 and 2 may be amended to incorporate a duration discriminating circuit arranged between the output of comparing circuit 27 and the input of AND circuit 23. Discrimination on the base of the train length may be particularly helpful in case of two or more operators attending simultaneously to the same patient. In this case, recognition of the operator who has caused the contact may be obtained if the various transmitting units generate, each, trains of pulses having preset lengths which are different from each other, and the receiving and processing unit is able to detect and discriminate the lengths of the continuous component of the received signals.

Figure 4:
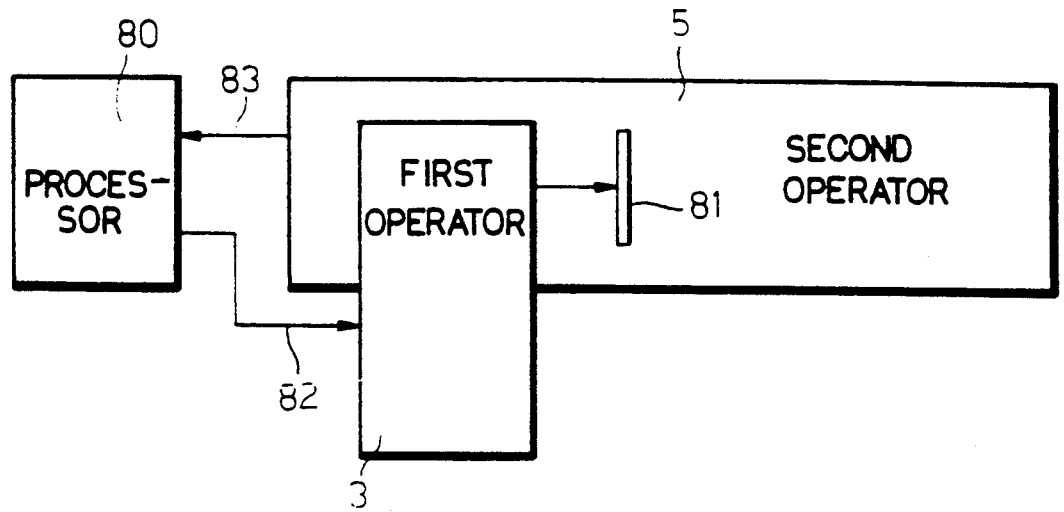
FIG. 4 shows a simplified block diagram of one component arrangement of the device according to the present invention.

Finally, the ground of transmitting unit/s 2, 2a, 2b, 2c may be connected to that of the receiving unit for obtaining a single voltage reference, in which case, all the components of the above units, with the exception of transducers 8, 8a, 8b, 8c, 11, may be housed in a single container from which the transducers project. This is shown in FIG. 4, wherein 3 and 5 indicate the first and second operator (in the example shown, the physician and patient); 80 indicates the processing unit including the signal generator (oscillator 7) and the incoming signal processing section (blocks 12-15 or 53-63) having a common ground; 81 indicates the potential contact medium (e.g. a glove); 82 indicates the line along which the signal from oscillator 7 is transmitted to a transducer (on first operator 3); and 83 indicates the line along which the signal from a receiver (on second operator 5) is transmitted to the processing section.

Figure 5:
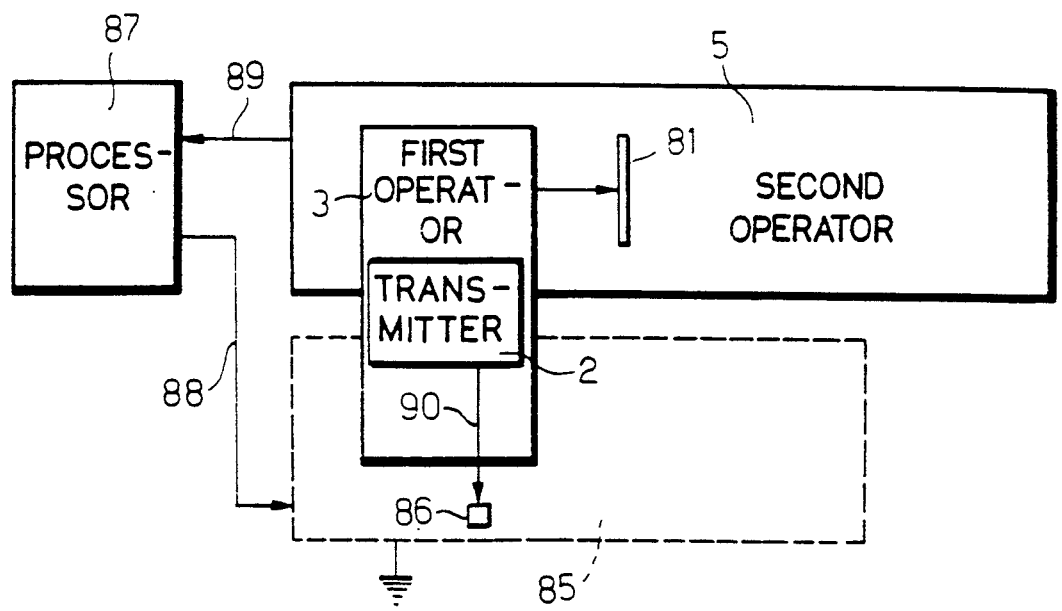
FIG. 5 shows a simplified block diagram of a variation of the FIG. 4 arrangement.

Alternatively, as shown in FIG. 5, transmitting unit 2, including signal generator 7 and transducer 8, may again be carried by first operator 3, and the common ground consist of a platform 85 on which operator 3 is stationed. In this case, 81 again indicates the potential contact medium; 5 indicates the second operator; 86 indicates contact, for example, on the sole or heel of the shoes of first operator 3; 87 indicates the incoming signal processing section; 88 indicates the line connecting section 87 to ground (platform 85); 89 indicates the line along which the signal from the receiver is transmitted to section 87; and 90 indicates the line connecting contact 86 to transmitting unit 2.

In both cases, unit 80 or 87 is capable of simultaneously monitoring several, e.g. four, operators 3.

We claim:

1. A device for detecting direct or indirect contact between at least one first operator (3) and a second operator (5), characterized by the fact that it comprises:
   means (7) for generating a predetermined signal having a frequency;
   first transducer means (8) for transmitting said predetermined signal to the body of said first operator (3);
   second transducer means (11) fittable to the body of said second operator (5) for picking up respective signals present in the said second operator and coupled thereto by capacitive and ohmic coupling; and processing means (12-15; 53-63) connected to said second transducer means (11), for analyzing the signals picked up by said second transducer means (11) for detecting and indicating the presence of a predetermined level of said predetermined signal.

2. A device as claimed in claim 1, characterized by the fact that said generating means comprises an oscillator (7).

3. A device as claimed in claim 2, characterised by the fact that said oscillator (7) generates an alternating signal having a predetermined frequency.

4. A device as claimed in claim 3, characterised by the fact that said predetermined frequency is within the audio frequency band.

5. A device as claimed in claim 1, characterized by the fact that said first and second transducer means (8, 11) substantially comprise at least one electrode for transmitting or picking up electrical potentials in relation to the body of said first and second operator (3, 5).

6. A device as claimed in claim 1, characterised by the fact that said processing means (12, 13, 14, 15) comprise a band-pass filter (12) connected downstream from said second transducer means (11).

7. A device as claimed in claim 1, characterised by the fact that said processing means (12, 13, 14, 15) comprise at least a circuit (13) for processing said signal picked up by said second transducer means (11); said circuit (13) having means (25, 26) for converting said signal into a continuous signal, and means (27) for comparing said continuous signal with a predetermined reference value.

8. A device as claimed in claim 7, characterised by the fact that said processing circuit (13) comprises means (29) for clipping said signal picked up by said second transducer means (11); the output of said clipping means (29) being connected to enabling means (23) only activated by said comparing means (27) if the amplitude of said continuous signal exceeds said predetermined reference value.

9. A device as claimed in claim 1, characterised by the fact that said processing means (12, 13, 14, 15) comprise at least a check circuit (14) for determining whether the frequency of said signal picked up by said second transducer means (11) substantially matches the frequency of said signal produced by said generating means (7).

10. A device as claimed in claim 9, characterised by the fact that said check circuit (14) substantially consists of a phase locked loop.

11. A device as claimed in claim 1, characterised by the fact that said processing means comprise an analog-digital converter (55) for converting said signal picked up by said second transducer means (11) into a digital signal; and digital processing means (56-62) for receiving said digital signal and detecting the significant presence of said predetermined signal.

12. A device as claimed in claim 11, characterised by the fact that said digital processing means comprise first means (60) for comparing said digital signal with a predetermined reference value; and second means (61) for comparing said digital signal with a predetermined time curve.

13. A device as claimed in claim 12, characterised by the fact that it comprises a memory (62) for storing said predetermined time curve; and that said second comparing means (61) present an enabling input connected to the output of said first comparing means (60).

14. A device as claimed in claim 12, characterised by the fact that said first and second comparing means (60, 61) are implemented via a microprocessor (59).

15. A device as claimed in claim 12, characterised by the fact that said digital processing means also comprise a selective digital filter (57) connected downstream from said converter (55); and an effective value detector (58) connected downstream from said digital filter and upstream from said first and second comparing means (60, 61).

16. A device as claimed in claim 15, characterised by the fact that said digital filter (57) and said detector (58) are implemented via a programmable device (56) operating as a digital, variable-band filter and tunable to the frequency of said generating means (2), and subsequently as a detector for detecting the effective value of the output signal from said digital filter.

17. A device as claimed in claim 1, characterised by the fact that said processing means (12-15; 53-62) comprise signaling means (15, 15') for indicating the significant presence of said signal picked up by said second transducer means (11); said signaling means (15, 15') comprising optical (33; 63) and/or acoustic (35) signaling elements.

18. A device as claimed in claim 17, characterised by the fact that said signaling means (15) present means (31, 32) for intermittently controlling said signaling elements (33, 35) for a predetermined length of time.

19. A device as claimed in claim 18, characterised by the fact that said control means (31, 32) substantially consist of a monostable circuit (31) and an astable circuit (32) connected downstream from said monostable circuit (31); the output of said astable circuit (32) controlling said signaling elements (33, 34).

20. A device as claimed in claim 17, characterized by the fact that said signaling means (15) are enabled by a check circuit (14) for determining whether the frequency of said signal picked up by said second transducer means (11) substantially matches the frequency of said signal produced by said generating means.

21. A device as claimed in claim 1, characterised by the fact that it comprises mass storage means (66) connected to said processing means (53-63), for storing said signals as well as alarm signals generated by said processing means (53-63).

22. A device as claimed in claim 1, characterised by the fact that it comprises display means including a monitor (65) connected to said processing means (53-63), for displaying said signals picked up by said second transducer means (11) as well as alarm signals generated by said processing means (53-63).

23. A device as claimed in claim 1, characterised by the fact that said generating means (7) and said processing means (12-15; 53-66) are connected to a line having a common reference potential (85).

24. A device as claimed in claim 23, characterised by the fact that said line consists of a platform (85).

25. A device as claimed in claim 1, characterized in that said generating means (7) generates a train of pulses of preset length and in that said processing means (12-15; 53-63) comprises length discrimination means for detecting the length of a received train of pulses and comparing the detected length with said preset length.

* * * * *